United States Patent
Livingston (10) Patent No.: US 6,716,352 B1
(45) Date of Patent: Apr. 6, 2004

(54) METHOD FOR REMOVING AND RECOVERING AROMATIC AMINES BY USING A NON-POROUS MEMBRANE

(75) Inventor: Andrew Guy Livingston, London (GB)

(73) Assignee: Membrane Extraction Technology Limited (GB)

(*) Notice: Subject to any disclaimer, the term of this patent is extended or adjusted under 35 U.S.C. 154(b) by 92 days.

(21) Appl. No.: 10/031,537

(22) PCT Filed: Jul. 21, 2000

(86) PCT No.: PCT/GB00/02827

§ 371 (c)(1),
(2), (4) Date: Jan. 18, 2002

(87) PCT Pub. No.: WO01/09042

PCT Pub. Date: Feb. 8, 2001

(30) Foreign Application Priority Data

Jul. 30, 1999 (GB) .............................................. 9918031

(51) Int. Cl.⁷ ........................ B01D 61/00; B01D 61/36; B01D 61/38; B01D 71/00; C02F 1/44
(52) U.S. Cl. ........................ 210/634; 210/640; 210/644; 210/490; 210/500.1
(58) Field of Search ................................ 210/634, 640, 210/644, 649, 490, 500.1

(56) References Cited

U.S. PATENT DOCUMENTS 5,507,949 A * 4/1996 Ho .............................. 210/490
5,552,053 A * 9/1996 Ho et al. ...................... 210/640
5,585,004 A 12/1996 Livingston ................... 210/651

FOREIGN PATENT DOCUMENTS

| EP | 0 485 077 A1 | 5/1992 |
| GB | 2 333 473 A | 7/1999 |
| WO | WO 00/00275 | 1/2000 |

* cited by examiner

Primary Examiner—John Kim
(74) Attorney, Agent, or Firm—Fay, Sharpe, Fagan, Minnich & McKee, LLP (57) ABSTRACT

A process for removing and recovering undissociated aromatic amines dissolved in aqueous fluid comprises the steps of (a) transferring undissociated aromatic amines from the aqueous fluid to an acidic stripping solution across a membrane wherein the membrane is a non-porous, selectively permeable membrane; (b) regulating the volume of acidic stripping solution employed relative to the volume of aqueous fluid treated so that the total aromatic amine concentration in the acidic stripping solutions, comprising the sum of the dissociated and undissociated aromatic amine concentrations, is above the solubility of the aromatic amine in water; (c) regulating the pH of the acidic stripping solution in contact with the membrane so that the membrane remains selectively permeable; (d) adjusting the pH of the aromatic amine containing acidic stripping solution to a value above the acidic dissociation constant of the aromatic amine and (e) separating the resulting aromatic amine and the acidic stripping solution.

32 Claims, 6 Drawing Sheets

Figure 1 - Aromatic amine recovery process

Figure 2- Aromatic amine recovery process with bundle of tubular membranes

Figure 3- Aromatic amine recovery process with elastomeric tube membrane

Figure 4- aromatic amine recovery process with elastomeric tube membrane and pH control Figure 5 - Aromatic amine recovery process operated with a well mixed stripping solution recirculated at high rate to a remote membrane module.

Figure 6 - Two stage aromatic amine recovery process

METHOD FOR REMOVING AND RECOVERING AROMATIC AMINES BY USING A NON-POROUS MEMBRANE

The present invention relates to a process for the removal and recovery of one or more aromatic amines from an aqueous fluid. In particular the process comprises transferring the aromatic amines from the aqueous fluid to an acidic stripping solution across a non porous, selectively permeable membrane, adjusting the pH of the acidic stripping solution and separating the resulting aromatic amine from the acidic stripping solution.

Many organic bases, such as aniline, toluidine, nitroaniline, enter aqueous process streams in chemical processing. These molecules are in many cases toxic. Methods for removing toxic organic molecules from aqueous process streams are well known. Some of these methods use membranes.

Membrane solvent extraction using microporous membranes to provide a phase contacting between aqueous and organic streams is well known. For example Kiani, Bhave and Sirkar Journal of Membrane Science 20 (1984) pp 125–145 report the use of microporous membranes for immobilising solvent interfaces during solvent extraction. Tompkins, Micheals and Peretti Journal of Membrane Science 75 (1992) pp 277–292 report using microporous polypropylene fibres to stabilise phase interfaces during extraction of nitrophenol from an aqueous solution into octanol. U.S. Pat. No. 5,512,180 describes a process wherein polypropylene glycol MW 4000 was used to extract nitrophenol in a microporous membrane contractor.

A continuing problem with membrane supported solvent extraction with microporous membranes is the breakthrough of one phase into the other due to pressure imbalances. To overcome this problem, various improvements have been suggested such as using composite membranes comprising a thin layer of non-porous organic-permeable polymer bound to a microporous membrane to avoid phase breakthrough, for example U.S. Pat. No. 4,960,520. However, in all of these processes a solvent phase containing the organic compound is produced which must then be disposed of or treated in some way. Contacting two aqueous streams with opposite sides of a membrane to effect extraction of organic pollutants from one side to the other is also known in the art. Supported liquid membranes have been applied in this mode. For example U.S. Pat. No. 5,507,949 describes a process wherein the pores of a microporous hydrophobic membrane are filled with a hydrophobic polyamphiphilic oligomeric or polymeric liquid to allow transport of various organics across the membranes. In this application the driving force for extraction across the supported liquid membranes may be provided by a stripping solution. The driving force produced by a stripping solution may rely upon conversion of an organic acid to its corresponding salt using a basic stripping solution, or conversion of an organic base to its corresponding salt using an acidic stripping solution. Biologically active stripping solutions may also be utlised, for example U.S. Pat. No. 4,988,443 to Michaels et al. discloses a method for contacting an aqueous waste stream containing organic toxicants with a nutrient-containing aqueous stream using hollow fibre membranes with water immiscible solvent filled pores. The two streams do not mix but the organic toxicants are transferred from the waste stream across the membrane to the nutrient stream. Microorganisms growing associated with the outside of the hollow fibres utilise the nutrients and organic toxicants as growth substrates which provides the driving force for continued transport.

In further applications non-porous membranes have been employed to effect extraction of organic molecules from one aqueous stream into another. U.S. Pat. No. 5,552,053 discloses solid polyamphiphilic polymer films used for keeping separate two aqueous phases, one being a waste stream and the other a stripping solution in which the organic pollutant can be concentrated by conversion into an ionised form at controlled pH.

In the above prior art, membranes are substantially rigid and are employed in shell and tube modules, in plate and frame modules, or in spiral wound modules. These modules are designed to generate good mass transfer and fluid distribution around all of the membrane surfaces.

In a few cases, tubular elastomeric non-porous homogeneous membranes for example silicone rubber (cross linked polydimethoxysiloxane) tubes have been disclosed. The tubular elastomeric membranes provide separation by allowing specific chemical species (for example, hydrophobic organic molecules such as benzene, toluene, or their derivatives) to preferentially dissolve in the membrane and permeate across the membrane by diffusion under the influence of a chemical activity driving force. For example, U.S. Pat. No. 5,585,004 to Livingston discloses a system of apparatus and method wherein a waste stream containing toxic organic compounds is fed to the inside of selectively permeable silicone rubber membrane tubes suspended in a bioreactor receptacle filled with a biologically active medium. The toxic organic compounds diffuse across the silicone rubber membrane and into the biologically active medium where they are destroyed by the microbial culture.

Further examples of the use of tubular elastomeric membranes are oxygenation of microbial systems (Cote et al, Journal of Membrane Science 1989 47 p107), and pervaporation (Raghunath and Hwang, Journal of Membrane Science 1992 65 p147). In the field of chemical analysis, silicone rubber membranes have been used to extract organics from aqueous streams prior to analysis (U.S. Pat. No. 4,715,217; U.S. Pat. No. 4,891,137).

The processing of organic-laden stripping solutions comprising organic acids in dissociated form in an aqueous solution is known with regard to nitrophenolic compounds recovery. For example, various processes are known in the art for disposing of stripping solutions containing nitrophenolic materials. These stripping solutions are generated as a by-product of nitration reactions. U.S. Pat. No. 4,597,875 discloses a process for removing the nitrophenolic materials from an alkaline stripping solution by treating the wastewater with an acid to lower its pH and convert the nitrophenolic compounds to a water insoluble solid material which is separated out of the wastewater and can be disposed of by incineration. U.S. Pat. No. 4,925,565 discusses a process in which the alkaline stripping solution is treated with acid to lower its pH, following which a substantially water insoluble solvent is used to extract the nitrophenolic compounds from the wastewater at elevated temperature. The solvent is recovered by distillation and the residue containing nitrophenolics can be incinerated. In variations on U.S. Pat. No. 4,925,565, the same inventors use differential control of the pH to recover specific nitrophenolic fractions by solvent extraction (U.S. Pat. No. 4,986,917) and precipitation (U.S. Pat. No. 4,986,920). However, the recovery of the nitrophenolic fraction is complicated by the fact that the nitrophenols form solid precipitates upon acidification of alkaline wastewater containing ionised nitrophenolic compounds at concentrations above the saturation concentration of non-ionised nitrophenolic compounds in water.

In the prior art utilising membranes for organics removal, the focus has been on the use of alkaline stripping solutions to remove organic acids from aqueous fluids. Many polymeric membrane materials and in particular elastomers have good resistance to alkalis. However, when it is desired to remove organic bases such as aromatic amines using acidic stripping solutions, problems can arise due to the lack of chemical resistance of many polymeric membrane materials, in particular elastomers, to mineral acids.

The present invention addresses the problems of the prior art

In one aspect the present invention provides a process for removing and recovering one or more undissociated aromatic amines dissolved in aqueous fluid, the process comprising the steps of: (a) transferring the one or more undissociated aromatic amines from the aqueous fluid to an acidic stripping solution, wherein transfer of the one or more undissociated aromatic amines from the aqueous fluid to the acidic stripping solution occurs across a membrane; wherein the membrane is a non porous, selectively permeable membrane; (b) regulating the volume of acidic stripping solution employed relative to the volume of aqueous fluid treated so that the total aromatic amine concentration in the acidic stripping solution, comprising the sum of the dissociated and undissociated aromatic amine concentrations, is above the solubility of the aromatic amines in water; (c) regulating the pH of the acidic stripping solution in contact with the membrane so that the membrane remains selectively permeable; (d) adjusting the pH of the aromatic amine containing acidic stripping solution to a value above the acidic dissociation constant of the aromatic amine and (e) separating the resulting aromatic amine and the acidic stripping solution.

By the term "selectively permeable" it is meant a membrane which is permeable to the undissociated aromatic amine and which is impermeable to the dissociated aromatic amine.

It will be appreciated that the term "aromatic amine" includes any compound of the formula $R^1NR^2R^3$ wherein $R^1$ is or comprises an aromatic group and $R^2$ and $R^3$ are independently selected from H or a hydrocarbyl group, such an alkyl or an aryl group. In this aspect an undissociated aromatic amine is a compound of the formula $R^1NR^2R^3$ and a dissociated aromatic amine is a compound of the formula $R^1NR^2R3H_+$.

Step (c) requires that the pH of the acidic stripping solution in contact with the membrane is regulated so that the membrane and selectively permeable. By this it is meant that the pH should be regulated so that the membrane materials are not rendered unusable through attack by the acidic stripping solution.

The present inventors have found that control of the pH in the acidic stripping solution assists in the reducing of costs and in increasing the membrane lifetime, particularly in respect of acidic stripping solutions.

In the present invention, aromatic amines present in an aqueous fluid in undissociated form are recovered by means of membrane extraction across a membrane. The membrane contains at least one non porous, selectively permeable layer. The aromatic amines pass into an acidic stripping solution in which the aromatic amines undergo dissociation. The acidic stripping solution is then further processed by adjusting the pH upwards until the aromatic amines re-associate and precipitate out of solution as liquids or solids.

Aromatic amines will undergo a dissociation reaction when the pH of the stripping solution is below the pKa= (14-pKb) of the aromatic amine, where pKb is the basicity constant and is defined as follows (see for example "Organic Chemistry" third Edition by T. W. G. Solomns, John Wiley and Sons, pp 836–837):

$$R\text{---}NH_2 + H_2O \rightleftharpoons RNH_3^+ + OH^- \qquad (1)$$

$$pKb = \log_{10}\left(\frac{[RNH_3^+][OH^-]}{[RNH_2]}\right) \qquad (2)$$

where R is an aromatic group containing organic structure.

The aromatic amine containing acidic stripping solution is subsequently neutralised to alkaline pH and the aromatic amines return to undissociated form and precipitate out of solution as organic liquids or solids. The organic liquids or solids are separated from the acidic stripping solution. The separated acidic stripping solution may contain saturation levels of undissociated aromatic amines and may be cycled back to the aqueous fluid to undergo further stripping. In the present invention the extraction and acidic stripping solution regeneration stages are integrated so that the streams leaving the process are pure organic liquid and treated aqueous waste respectively.

Preferably the aqueous fluid is an aqueous process stream.

Preferably the aqueous fluid is contacted with one side of the membrane and wherein the acidic stripping solution is contacted with the other side of the membrane. In a more preferred aspect prior to adjusting the pH of the aromatic amine containing acidic stripping solution, the acidic stripping solution is removed from contact with the membrane.

Preferably the acidic stripping solution separated in step (e) is recycled to the aqueous fluid prior to contact with the membrane. In one preferred alternative the acidic stripping solution separated in step (e) is recycled to the aromatic amine containing acidic stripping solution prior to removing the acidic stripping solution from contact with the membrane.

The resulting aromatic amine of step (e) may be a liquid or a solid.

The membrane of the present invention can be configured in accordance with any of the designs known to those skilled in the art, such as spiral wound, plate and frame, shell and tube, and derivative designs thereof. The membranes may be of cylindrical or planar geometry.

For shell and tube designs, the membrane comprises one or more tubular membranes each of which has an internal surface which defines an internal volume. In this aspect either the aqueous fluid or the acidic stripping solution is held within the internal volume of the tubular membrane(s) and the other of the aqueous fluid or the acidic stripping solution is in contact with the external surface of the tubular membrane(s). For spiral wound designs, either the aqueous fluid or the acidic stripping solution is within the membrane leaves and the other of the aqueous fluid or the acidic stripping solution is in contact with the external surface of the membrane leaves.

It will appreciated that in an industrial setting preferably the aqueous fluid is held within the internal volume of the tubular membrane(s) and the acidic stripping solution is in contact with the external surface of the tubular membrane(s), and wherein the tubular membrane(s) and the acidic stripping solution are operably contained.

The membrane of the present invention is formed from or comprises a material suitable to provide a non-porous, selectively permeable membrane. The membrane may consist of a homogeneous membrane such as a tube or sheet of material, or a composite membrane. The composite membrane may comprise a non-porous, selectively permeable layer and one or more further materials or may comprise a mixture of materials. The non-porous, selectively permeable layer or material prevents direct contact of the aqueous stream with the acidic stripping solution. This is important. If a direct contact stripping device such as a packed or plate column or microporous membrane contractor is used, the two streams would mix and there would be no resulting separation.

In a preferred aspect the membrane or the non-porous, selectively permeable layer thereof is formed from or comprises a material selected from modified polysiloxane based elastomers including polydimethylsiloxane (PDMS) based elastomers, ethylene-propylene diene (EPDM) based elastomers, polynorbornene based elastomers, polyoctenamer based elastomers, polyurethane based elastomers, butadiene and nitrile butadiene rubber based elastomers, natural rubber, butyl rubber based elastomers, polychloroprene (Neoprene) based elastomers, epichlorohydrin elastomers, polyacrylate elastomers, polyethylene, polypropylene, polytetrafluoroethylene (PTFE), polyvinylidene difluoride (PVDF) based elastomers, and mixtures thereof.

In a preferred aspect the membrane comprises a reinforcing material selected from an external mesh and support. This is particularly advantageous for homogenous tubes or sheets. Such tubes or sheets may be reinforced to increase their burst pressure, for example by overbraiding tubes using fibres of metal or plastic, or by providing a supporting mesh for flat sheets.

When the membrane comprises a non-porous layer and an additional component, the additional component may be a supporting layer. The supporting layer may be a porous support layer. Suitable materials for the open porous support structure are well known to those skilled in the art of membrane processing. Preferably the porous support is formed from or comprises a material selected from polymeric material suitable for fabricating microfiltration, ultrafiltration, nanofiltration or reverse osmosis membranes, including polyethylene, polypropylene, polytetrafluoroethylene (PTFE), polyvinylidene difluoride (PVDF) polyethersulfone, and mixtures thereof.

Preferably the tubular membranes have a high length to diameter ratios for example the tubular membranes may have an internal diameters from 0.5 to 5.0 mm, and/or a wall thicknesses between 0.1 and 1.0 mm and/or a length of from 50 to 500 meters. The length to diameter ratio of the tubular membrane may be from $1\times10^4$ to $1\times10^6$.

High length to diameter ratio such a those given above are considerably longer than the length to diameter ratios of membranes typically applied in prior art membrane extraction processes, and have the advantage that the aqueous fluid entering the membrane tubes passes down a long flow path before emerging from the membrane. Thus it is possible to remove a high percentage of the aromatic amine contaminants in one pass down a single membrane tube, and this reduces the need for extensive manifolding which arises when the aqueous fluid must be passed through several or many membrane modules to achieve the desired degree of removal. This reduction in manifolding results in cost advantages over shorter membrane tube.

In a further preferred aspect of the present invention a pH control system is used to regulate the flow of acidic stripping solution which contacts the membrane.

Control of pH in the acidic stripping solution is important. Upon contact with the membrane the acidic stripping solution pH will tend to be increased by the dissociation of the aromatic amine, and it is advantageous for the process efficiency that the pH of the acidic stripping solution is kept at least 0.5 pH units below the pKa of the aromatic amine. This may be achieved by fixing the flowrate and strength of the acidic stripping solution so as to ensure that this condition is always met. A higher acid concentration in the acidic stripping solution for given volumes or flows of aqueous fluid and acidic stripping solution will meet this condition better than a lower concentration of acid. A higher acid concentration also makes possible a lower acid flowrate for a given aromatic amine loading in the aqueous fluid; this results in a lower recycle stream flowrate from step (e), and hence a more cost effective system. However use of excessive acid in the acidic stripping solution will require excess alkali in the recovery stage. Also, excessively strong acids may damage the non-porous membrane. For example, silicone rubber is one of the most permeable elastomers and so desirable for use in the process, but can be damaged by acid concentrations above 1 wt. % mineral acid.

Preferably the stripping solution in contact with the nonporous membrane is well mixed so that its composition is well mixed throughout the volume operably in contact with the nonporous membrane.

Preferably the pH of the acidic stripping solution in contact with the non-porous membrane is controlled so that it is substantially the same throughout the acidic stripping solution in contact with the non-porous membrane separating layer.

Preferable the aqueous fluid contains an aromatic amine selected from aniline, chloroanilines, dichloroanilines, toluidines, dimethylaniline, nitroaniline, phenylaniline, methylaniline, etlylaniline, anisidine, benzylamine, fluoroanilines, difluoroanilines, aminophenols, and mixtures thereof.

Preferably the acidic stripping solution comprises a mineral acid selected from hydrochloric acid, sulphuric acid, phosphoric acid, nitric acid, and mixtures thereof.

Preferably the pH of the aromatic amine containing acidic stripping solution is adjusted in step (d) by the addition of alkali.

Preferably the alkali is an aqueous solution of an alkali selected from sodium hydroxide, sodium carbonate, calcium hydroxide, calcium carbonate, potassium hydroxide, potassium carbonate, and mixes thereof.

In a further preferred aspect the aqueous fluid is contacted with one side of a plurality of membranes in series, in parallel or in a combination thereof, and wherein the acidic stripping solution is contacted with the other side of each of the plurality of membranes.

The process may be performed in a continuous, semi-continuous or discontinuous (batch mode) manner. In the latter aspect the flow of at least one of the aqueous fluid, the acidic stripping solution, and the alkali solution is discontinuous.

In one aspect the resulting aromatic amine of step (e) is contacted with an organic solvent and subsequently treated in a further process. In this aspect it may be desirable to contact the amine containing acidic stripping solution and/or the separated aromatic amine with a solvent or solvent mixture in step (e). This may be particularly useful when the separated aromatic amine is a solid. The solvent introduced may dissolve the solid. This may be further useful when this solid is a product or reactant in a reaction and where the solid and the solvent used to dissolve the solid can be sent to the further process in which the solid material is produced or consumed.

The process of the present invention may be performed in a reactor comprising at least a first zone, a second zone, a third zone, and a fourth zone; wherein each of the zones is discrete from each other zone; wherein the first zone and the second zone are separated by the non porous membrane; wherein the first zone contains the aqueous fluid; wherein the second zone and fourth zone contain the acidic stripping solution; wherein the third zone contains amine containing acidic stripping solution; wherein the first zone and the third zone are operably connected to each other; wherein the second zone is operably connected to the third zone and the fourth zone; and wherein the acidic stripping solution is circulated between the fourth zone and the second zone such that the acidic stripping solution is well mixed throughout its volume.

Preferably, the acidic stripping solution is circulated between the fourth zone and the second zone at a high rate relative to the flow of aqueous fluid. By the term "high rate" it is preferably meant that the volume of acidic stripping solution contacted with the membrane is greater than the volume of aqueous fluid contacted with the membrane. The ratio of acidic stripping solution volume to aqueous fluid volume contacted with the membrane may be >2:1.>5:1, or >10:1.

The aqueous fluid and/or the acidic stripping solution of the present invention may be heated before contact with the membrane. The aqueous fluid and/or the acidic stripping solution of the present invention may have a temperature above room temperature (25° C.). This may increase the rate of mass transfer across the non-porous membrane.

In a further preferred aspect the aqueous fluid contains substantial quantities of dissolved inorganic or organic materials. By the term "substantial quantities" it is meant greater than 0.1 wt %. The inorganic materials may include salts, such as sodium chloride, potassium chloride and mixtures thereof. The organic materials may include solvents, such as methanol, ethanol, acetone, acetate and mixtures thereof.

The aromatic amine in the acidic stripping solution dissociates according to an equilibrium reaction described by equation (1). Even at low pH, there will be some finite fraction of the aromatic amine present in dissociated form, and the total aromatic amine concentration will be equal to the sum of the concentration of dissociated and the concentration of undissociated aromatic amine. In general, the higher the concentration of total aromatic amine in the acidic stripping solution at a given pH, the higher will be the concentration of undissociated aromatic amine. This undissociated aromatic amine will act to reduce the driving force for mass transfer of undissociated aromatic amine from the aqueous fluid to the acidic stripping solution. This effect will be relatively greater for the aqueous fluid in the section of membrane near the point of exit of the aqueous fluid from the membrane.

Thus in a further preferred embodiment of the present invention, it is desirable to use two well mixed stripping stages in series. In this embodiment, the aqueous fluid first contacts a membrane whose other side is in contact with a well mixed strength 1 acidic stripping solution in a first stripping stage, and then contacts a second membrane. Whose other side is in contact with a well mixed strength 2 acidic stripping solution in a second stage. Strength of an acidic stripping solution is determined by the strength of the acid, for example, the mineral acid, fed to the acidic stripping solution. In this aspect, the mineral acid concentration fed to stripping solution 1 is stronger than the mineral acid concentration fed to stripping solution 2. The aqueous fluid passes from the membrane of stripping stage 1 to membrane of stripping stage 2. Mineral acid is fed to the acidic stripping solution in stripping stage 2, and the resulting strength 2 stripping solution from stage 2 is passed into stage 1 where further mineral acid is added to increase the strength of the acidic stripping solution in stage 1 to strength 1. The total aromatic amine concentration in stage 1 is greater than the total aromatic amine concentration in stage 2. The pH may be controlled to be constant in each stripping stage and may be set at different values in stage 1 and stage 2. The use of more than two stages is also envisaged.

The invention will now be described, by way of example only, with reference to the accompanying drawings, in which.

Figure 1:
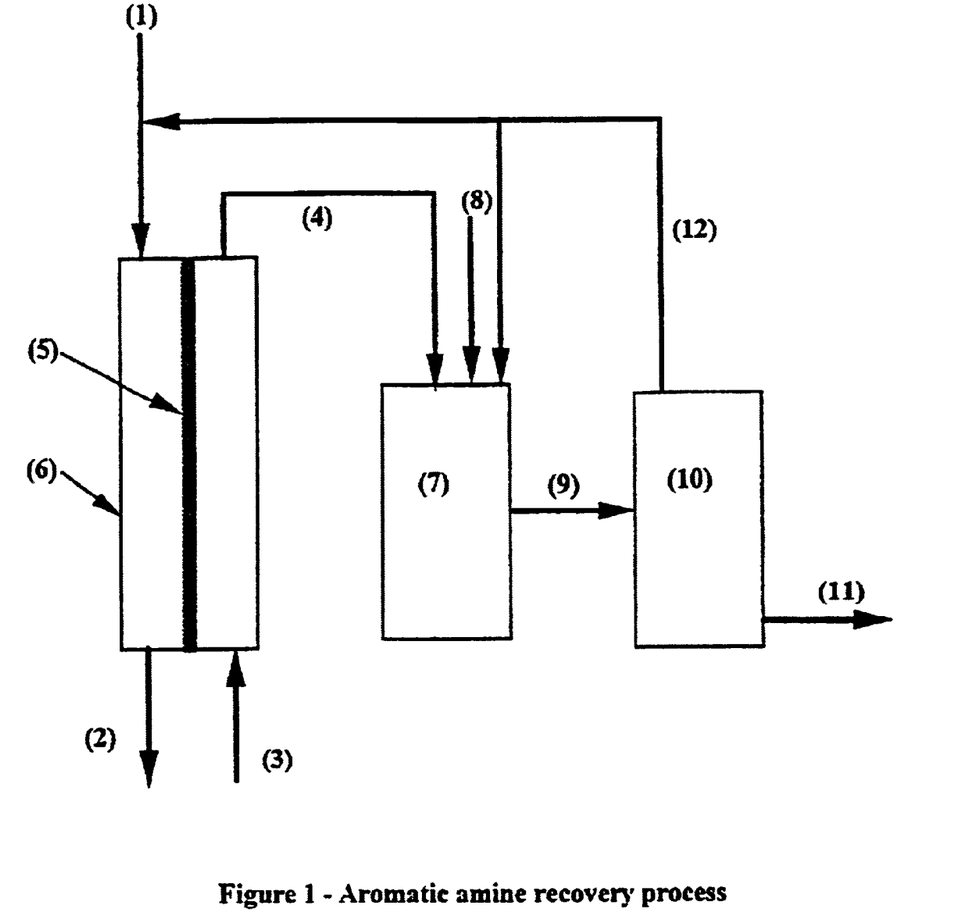
FIG. 1 is a schematic of an apparatus operating the process of the present invention.

FIG. 1 shows a schematic of one embodiment of the process. The aqueous fluid containing undissociated aromatic amines (1) passes on one surface of a membrane containing at least one nonporous separating layer (5), optionally mounted in a membrane module (6). Undissociated aromatic amines in the wastewater across the membrane into the acidic stripping solution (3), whose pH is such that the aromatic amines are converted into their corresponding salts. The aqueous fluid exiting the membrane has a reduced concentration of aromatic amines relative to the aqueous fluid (1) entering the membrane. The aromatic amine laden acidic stripping solution (4) leaves the membrane module (6) containing dissociated aromatic amines and enters a neutralisation vessel (7). By manipulation of the ratio between the volume of aqueous stream fed (1) and volume of acidic stripping solution fed (3), i.e. by using a ratio greater than 1, the concentration of dissociated aromatic amines in aromatic amine laden acidic stripping solution (4) is elevated to levels higher than the saturation concentration of undissociated aromatic amines in water. In the neutralisation vessel (7) a mineral alkali (8) is added to adjust pH of the solution to a value above the pKa of the aromatic amine. This converts the aromatic amine back to an undissociated form. Since it is at a concentration higher than the saturation concentration of undissociated amine in water, the aromatic amine precipitates out of solution as a liquid or solid. The neutralisation vessel (7) may be optionally stirred. The resulting two phase mixture (9) is passed to a settling vessel (10) where the two phases are separated. The organic phase (either liquid or solid) is removed (11) from the settling vessel (10), and the aromatic amine saturated aqueous layer (12) is recirculated back either to the aqueous process stream (1), or to the neutralisation tank (7).

In a preferred embodiment, the membranes may comprise a bundle of tubular membranes with suitable head piece connections for allowing flow of the aqueous fluid to pass through the interior of the membranes. This bundle of tubular membranes may be suspended in a tank or other vessel so that the outside surface of the fibres is substantially immersed in the acidic stripping solution. In this case the acidic stripping solution will be mixed or agitated using a stirrer or pump or some other suitable device to ensure that the acidic stripping solution is well mixed at all times and the composition of the stripping solution in contact with the membrane will be the same as the concentration of the stripping solution (4) leaving the tank (15), FIG. 2 shows this general arrangement where a bundle of tubular membranes (13) are connected at each end to allow wastewater flow through headpieces (14), and are immersed in a tank (15) of acidic stripping solution.

Figure 3:
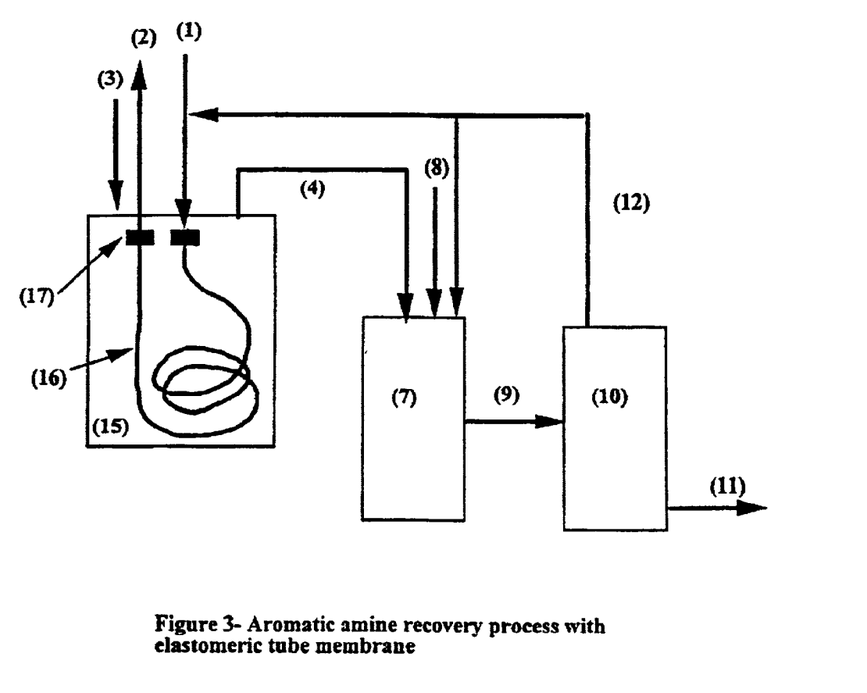
FIG. 3 is a schematic of an apparatus operating the process of the present invention.

FIG. 3 shows yet another preferred embodiment, in which one or more elastomeric tubular membranes (16) connected using suitable headpieces (17) are suspended in a well mixed tank (15) containing acidic stripping solution (4). The elastomeric tubular membranes can be coiled, stacked or otherwise arranged in the tank so that they have their surfaces substantially immersed in the acidic stripping solution (4). It is advantageous in this embodiment to use elastomeric tubular membranes which have high length to diameter ratios for example the elastomeric tubular membranes might have internal diameters from 0.5 to 5.0 mm, wall thicknesses between 0.1 and 1.0 mm and lengths from 50 to 500 meters, i.e. length to diameter ratios of $1 \times 10^4$ to $1 \times 10^6$.

Figure 2:
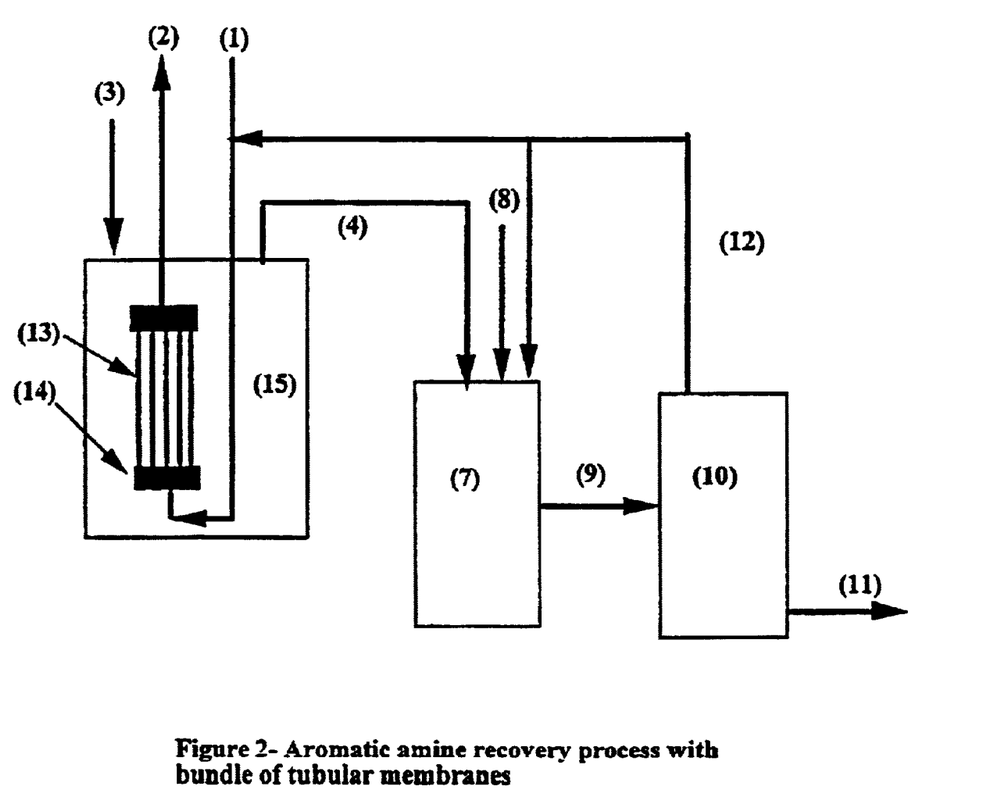
FIG. 2 is a schematic of an apparatus operating the process of the present invention.

The configurations illustrates in FIGS. 2 and 3 are made possible by the rapid dissociation reaction in the acidic stripping solution which removes the need to configure the flow over the outside surfaces of the membrane so as to provide high rates of film mass transfer.

It is apparent to one skilled in the art that it is desirable to use a strong acid (by way of non limiting example, hydrochloric acid above 20 wt. % (HCl), as a feed acidic stripping solution (3), while maintaining pH in the acidic stripping solution in contact with the non-porous membrane (4) separating layer at a high enough value to minimise the need for alkali addition and to ensure maximal lifetime of the non-porous membrane separating layer. It is with these objectives in mind that the configurations of FIGS. 2, 3, 4 and 5 are found to have advantages over passing the aqueous and organic streams in countercurrent flow through membrane modules as shown in FIG. 1. In the configurations of FIGS. 2, 3, 4 and 5 the acid added (3) can be concentrated but as it is immediately mixed into the aromatic amine laden acidic stripping solution (4) in the well mixed tank (15) the actual acid concentration of the acidic stripping solution in contact with the non-porous membrane separating layers can be everywhere substantially less than the acid concentration of the feed acidic stripping solution (3).

Figure 4:
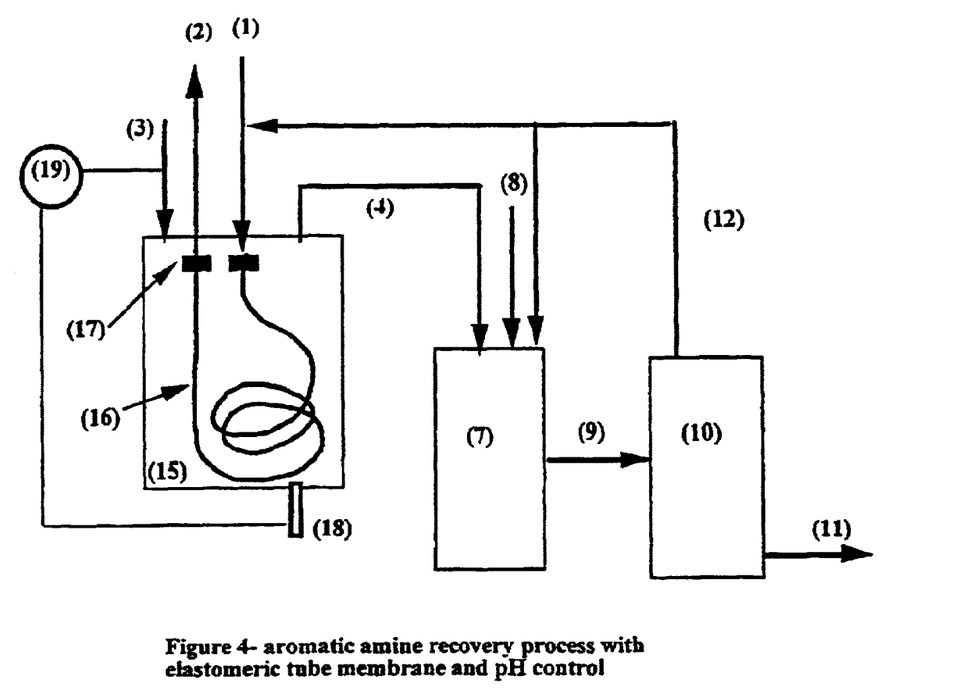
FIG. 4 is a schematic of an apparatus operating the process of the present invention.

A further preferred embodiment of the process as shown in FIG. 4 by way of non-limiting example can be employed. A well mixed tank (15) containing an elastomeric membrane tube (16) immersed in acidic stripping solution (4) has a pH sensor (18) in contact with the well mixed acidic stripping solution (4). This pH sensor measures pH and transmits this information to a control device (19) which regulates flow of feed acidic stripping solution (3) to the tank to hold pH at the desired value. Using this approach pH in the tank (15) can be controlled to the highest value consistent with good process efficiency, thus minimising acidity in the tank and in the aromatic amine laden acidic stripping solution (4). This has consequent advantages for neutralisation costs and membrane lifetime.

Figure 5:
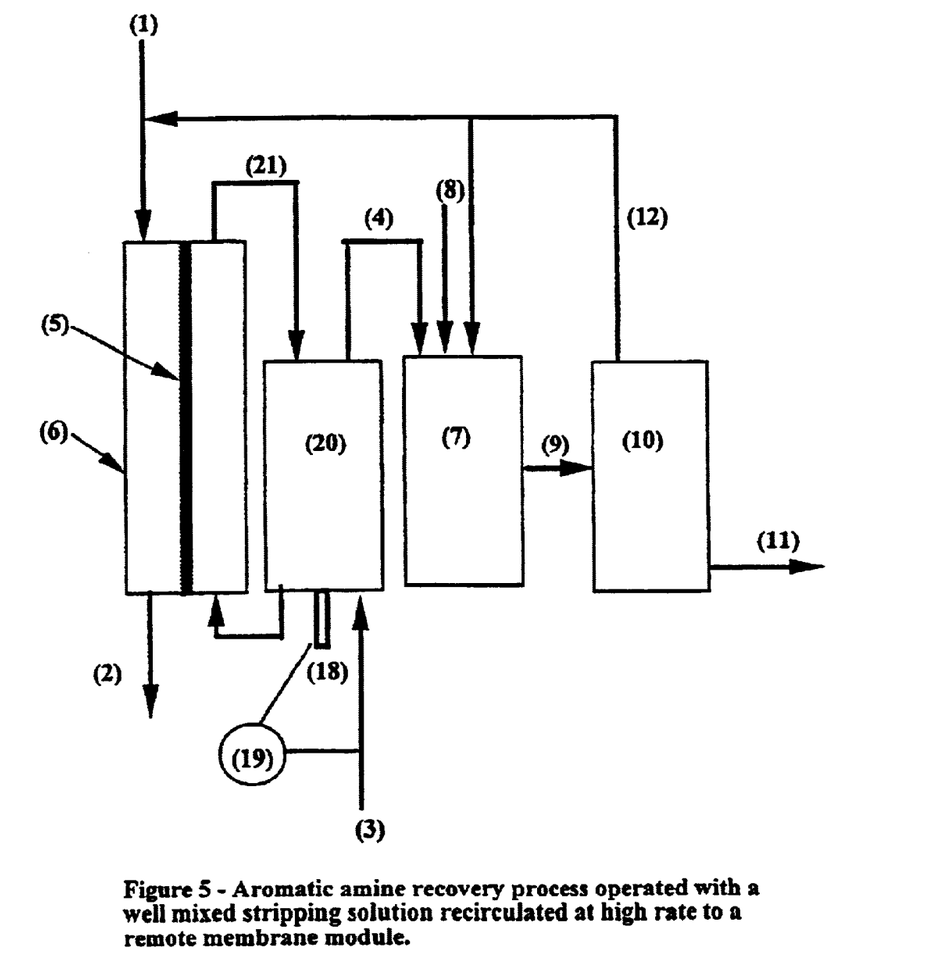
FIG. 5 is a schematic of an apparatus operating the process of the present invention.

In yet another preferred embodiment shown in FIG. 5, the advantages of a well mixed acidic stripping solution in a remote stripping tank (20) are shown in connection with the use of a membrane module of the type used in FIG. 1. The pH is controlled in the stripping tank by a pH sensor (18) and a control device (19) which regulates the flow feed acidic stripping solution (3) to the stripping tank (20). The acidic stripping solution is recirculated (21) to the membrane module or modules at a high rate so that for all practical purposes the acidic stripping solution can be considered well mixed throughout its volume. Aromatic amine laden acidic stripping solution is withdrawn (4) and passed to the neutralisation tank (7).

In yet another preferred embodiment the temperature of the acidic stripping solution in tank (15) or tank (20) and or the aqueous stream (1) can be increased above ambient conditions to increase the rate of mass transfer across the non-porous separating layer of the membrane.

Figure 6:
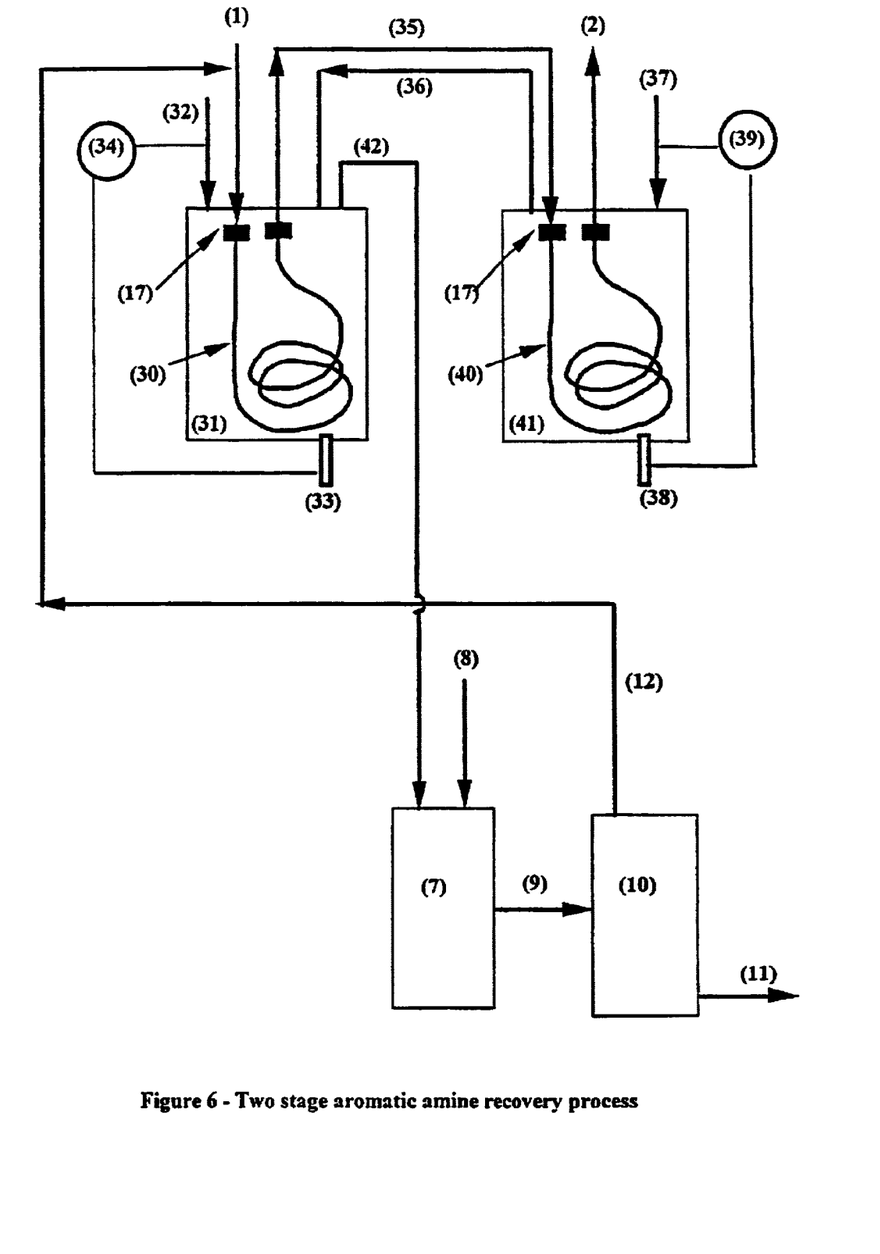
FIG. 6 is a schematic of an apparatus operating the process of the present invention.

In yet another preferred embodiment shown in FIG. 6, the use of two stripping stages is shown with two strengths of acidic stripping solution. The aqueous fluid (1) enters the first stripping stage in which a membrane (30) is suspended in the first stage tank (31). An acidic stripping solution containing acid (32) is added to the stage 1 tank (31) automatically by a pH controller (34) connected to a pH probe (33). The stripping solution in stage 1 is well mixed throughout the volume of the stage 1 tank (31) so that it is of identical composition to the stripping solution (42) exiting the stage 1 tank. The aqueous fluid (35) flows out of stage 1 and into stage 2 where a second membrane (40) is suspended in the stage 2 tank (41). The aqueous fluid (2) flows out of the second membrane (40) with a reduced concentration of aromatic amine relative to stream (1). In the second stage, acidic stripping solution containing mineral acid (37) at a lower concentration than stream (32) is added to the stage 2 tank (41) automatically by a pH controller (39) connected to a pH probe (38). The stripping solution in the stage 2 tank (41) is well mixed throughout the volume of the stage 2 tank so that it is of identical composition to the stripping solution (36) exiting the stage 2 tank. The stripping solution (36) exiting the stage 2 tank (41) is fed to the stage 1 tank (31). The system is configured and operated so that the total aromatic amine concentration in stream (36) is less than the total aromatic amine concentration in stream (42). The stripping solution (42) from the stage (1) tank is passed to the neutralisation vessel (7). Following phase separation, the aromatic amine saturated aqueous layer (12) is recirculated back to the aqueous fluid (1).

The processes described above may be operated continuously, semi-continuously or in batch mode. The tanks may be single tanks or multiples tanks. The neutralisation vessel (7) and the phase separating vessel (10) may be combined into the same vessel. Mixing of one or all of the tanks may be achieved by using any device known to those skilled in the art, such as mixers, pumps, or air lift devices. Variations and changes may be made by those skilled in the art without departing from the spirit of the invention.

The invention will now be described in further detail in the following non-limiting Examples.

EXAMPLES

Example 1

The following example describes batch operation of the present invention. 1000 mL of acidic stripping solution comprising a dilute solution of hydrochloric acid were added to a stirred tank containing a 13 meter length of a silicone rubber membrane tube with internal diameter of 3 mm, wall thickness 0.6 mm 20 liters of a wastewater containing 0.6 wt. % aniline were recirculated from a drum through the inside of the elastomeric membrane tube. Concentrated (37 wt. %) hydrochloric acid was added regularly to the acidic stripping solution to maintain pH in the range 1–4. After 14 days the experiment was stopped, and the acidic stripping solution removed. The pH of the acidic stripping solution was adjusted to 11 by addition of 40 wt. % NaOH solution, and a dark organic liquid formed and was separated. This organic liquid was analysed via gas chromatography and found to be more than 99% pure aniline.

Example 2

The following example describes continuous operation of the present invention. 1000 mL of acidic stripping solution were added to a stirred tank containing a 10 meter length of a silicone rubber membrane tube with internal diameter of 3 mm, wall thickness 0.6 mm. A pH sensor was suspended in the tank and a controller as connected to the sensor so as to add 37 wt. % hydrochloric acid to the tank when required to maintain pH. The controller held pH at 2.5+/−0.2 pH units. A flow of aqueous process stream containing aniline at 0.5 wt. % was pumped from a drum and passed through the inside of the membrane tube. The overflow of the acidic stripping solution was periodically removed to a tank where pH was adjusted, resulting in formation of a dark organic liquid. The resulting aqueous and organic phases were separated and the aqueous phase mixed with the aqueous process stream in the drum. The dark organic liquid was analysed and found to be aniline.

Example 3

The following example describes batch operation of the present invention used to recover 2,4 difluoroaniline from an aqueous stream. 1000 mL of strip solution comprising a dilute solution of hydrochloric acid were added to a stirred tank containing a 50 meter length of a silicone rubber membrane tube with internal diameter of 3 mm, wall thickness 0.6 mm 20 liters of a wastewater containing 0.35 wt % 2,4 difluoroaniline were recirculated from a drum through the inside of the elastomeric membrane tube. Concentrated (37 wt %) hydrochloric acid was added regularly to the strip solution to maintain pH in the range 1.5–2.0. After 4 days the experiment was stopped, and the strip solution removed. The pH of the strip solution was adjusted to 11 by addition of 40 wt % NaOH solution, and a dark organic liquid formed and was separated. This organic liquid was analysed via gas chromatogaphpy and found to be more than 99% pure 2,4 difluoroaniline.

Example 4

The following example describes batch operation of the process to recover a mixture of 2,4 difluoroaniline and 2,4,6 bromodifluoroaniline from an aqueous waste. 100 mL of strip solution comprising a 10% wt solution of hydrochloric acid were added to a stirred tank containing a 20 meter length of an EPDM rubber membrane tube with internal diameter of 3 mm, wall thickness 1 mm, 20 liters of a wastewater containing 0.35 wt % 2,4 difluoroaniline and 0.15 wt % 2,4,6 bromodifluoroaniline were recirculated from a drum through the inside of the elastomeric membrane tube. After 4 days the experiment was stopped, and the strip solution removed. The pH of the strip solution was adjusted to 11 by addition of 40 wt % NaOH solution, and a dark organic liquid formed and was separated. This organic liquid was analysed via gas chromatographpy and found to be more than 20% 2,4 difluoroaniline and 80% 2,4,6 bromodifluoroaniline.

All publications mentioned in the above specification are herein incorporated by reference. Various modifications and variations of the described methods and system of the invention will be apparent to those skilled in the art without departing from the scope and spirit of the invention Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

What is claimed is:

1. A process for removing and recovering one or more undissociated aromatic amines dissolved in aqueous fluid, the process comprising the steps of:
   (a) transferring the one or more undissociated aromatic amines from the aqueous fluid to an acidic stripping solution, wherein transfer of the one or more undissociated aromatic amines from the aqueous fluid to the acidic stripping solution occurs across a membrane: wherein the membrane is a non porous, selectively permeable membrane;
   (b) regulating the volume of acidic stripping solution employed relative to the volume of aqueous fluid treated so that the total aromatic amine concentration in the acidic stripping solution, comprising the sum of the dissociated and undissociated aromatic amine concentrations, is above the solubility of the aromatic amines in water;
   (c) regulating the pH of the acidic stripping solution in contact with the membrane so that the membrane remains selectively permeable;
   (d) adjusting the pH of the aromatic amine containing acidic stripping solution to a value above the acidic dissociation constant of the aromatic amine and
   (e) separating the resulting aromatic amine and the acidic stripping solution.

2. A process according to claim 1 wherein the aqueous fluid is an aqueous process stream.

3. A process according to claim 1 wherein the aqueous fluid is contacted with one side of the membrane and wherein the acidic stripping solution is contacted with the other side of the membrane.

4. A process according to claim 3 wherein prior to adjusting the pH of the aromatic amine containing acidic stripping solution, the acidic stripping solution is removed from contact with the membrane.

5. A process according to claim 3 wherein the acidic stripping solution separated in step (e) is recycled to the aqueous fluid prior to contact with the membrane.

6. A process according to claim 4 wherein the acidic stripping solution separated in step (e) is recycled to the aromatic amine containing acidic stripping solution prior to removing the acidic stripping solution from contact with the membrane.

7. A process according, to claim 1 wherein the resulting aromatic amine of step (e) is a liquid.

8. A process according to claim 1 wherein the resulting aromatic amine of step (e) is a solid.

9. A process according to claim 1 wherein the membrane is mounted in a plate and frame configuration, a shell and tube configuration, or a spiral wound configuration.

10. A process according to claim 1 wherein the membrane comprises one or more tubular membranes each of which has an internal surface which defines an internal volume and either the aqueous fluid or the acidic stripping solution is held within the internal volume of the tubular membrane(s) and the other of the aqueous fluid or the acidic stripping solution is in contact with the external surface of the tubular membrane(s).

11. A process according to claim 10 wherein the aqueous fluid is held within the internal volume of the tubular membrane(s) and the acidic stripping solution is in contact with the external surface of the tubular membrane(s), and wherein the tubular membrane(s) and the acidic stripping solution are operably contained.

12. A process according to claim 10 wherein the tubular membrane(s) is elastomeric.

13. A process according to claim 10 wherein the tubular membrane(s) has a length to diameter ratio of from 10,000 to 1,000,000.

14. A process according to claim 1 wherein the acidic stripping solution in contact with the nonporous membrane is well mixed throughout its volume such that its composition is uniform throughout.

15. A process according to claim 1 wherein the pH of the stripping solution in contact with the non-porous membrane is controlled so that it is substantially the same throughout the volume of acidic stripping solution in contact with the non-porous membrane separating layer.

16. A process according to claim 1 wherein the aqueous fluid contains an aromatic amine selected from aniline, chloroanilines, dichloroanilines, toluidines, dimethylaniline, nitroaniline, phenylaniline, methylaniline, ethylaniline, anisidine, benzylamine, fluoroanilines, difluoroanilines, aminophenols and mixtures thereof.

17. A process according to claim 1 wherein the acidic stripping solution comprises a mineral acid selected from hydrochloric acid, sulphuric acid, phosphoric acid, nitric acid, and mixtures thereof.

18. A process according to claim 1 wherein the pH of the aromatic amine containing acidic stripping solution is adjusted in step (d) by the addition of an alkali.

19. A process according to claim 18 wherein the alkali is an aqueous solution of an alkali selected from sodium hydroxide, sodium carbonate, calcium hydroxide, calcium carbonate, potassium hydroxide, potassium carbonate, and mixtures thereof.

20. A process according to claim 1 wherein the membrane is formed from or comprises a material selected from modified polysiloxane based elastomers, ethylene-propylene diene (EPDM) based elastomers, polynorbornene based elastomers, polyoctenamer based elastomers, polyurethane based elastomers, butadiene and nitrile butadiene rubber based elastomers, natural rubber, butyl rubber based elastomers, polychloroprene (Neoprene) based elastomers, epichlorohydrin elastomers, polyacrylate elastomers, polyethylene, polypropylene, polytetrafluoroethylene (PTFE), polyvinylidene difluoride (PVDF) based elastomers, and mixtures thereof.

21. A process according to claim 20 wherein the modified polysiloxane based elastomer is a polydimethylsiloxane (PDMS) based elastomer.

22. A process according to claim 1 wherein the membrane comprises a reinforcing material selected from an external mesh and support.

23. A process according to claim 1 wherein the membrane is a composite membrane comprising a porous support and at least one nonporous layer.

24. A according to claim 23 where the porous support is formed from or comprises a material selected from polymeric material suitable for fabricating microfiltration, ultrafiltration, nanofiltration or reverse osmosis membranes, including polyethylene, polypropylene, polytetrafluoroethylene (PTFE), polyvinylidene difluoride (PVDF) polyethersulfone, and lures thereof.

25. A process according to claim 1 wherein the aqueous fluid is contacted with one side of a plurality of membranes in series, in parallel or in a combination thereof, and wherein the acidic stripping solution is contacted with the other side of each of the plurality of membranes.

26. A process according to claim 1 wherein the process is performed in a continuous manner.

27. A process according to claim 19 wherein the flow of at least one of the aqueous fluid, the acidic stripping solution, and the alkali solution is discontinuous.

28. A process according to claim 1 wherein the resulting aromatic amine of step (e) is contacted with an organic solvent and subsequently treated in a further process.

29. A process according to claim 1 wherein the process is performed in a reactor comprising at least a first zone, a second zone, a third zone, and a fourth zone;

wherein each of the zones is discrete from each other zone;

wherein the first zone and the second zone are separated by the non-porous membrane;

wherein the first zone contains the aqueous fluid;

wherein the second zone and fourth zone contain the acidic stripping solution;

wherein the third zone contains amine containing acidic stripping solution;

wherein the first zone and the third zone are operably connected to each other;

wherein the second zone is operably connected to the third zone and the fourth zone; and wherein the acidic stripping solution is circulated between the fourth zone and the second zone such hat the acidic stripping solution is well mixer throughout its volume.

30. A process according w claim 29 wherein a pH control system is used to regulate the flow of acidic stripping solution between the fourth zone and the second zone.

31. A process according to claim 1 wherein at least one of the aqueous fluid and the acidic stripping solution has a temperature above room temperature.

32. A process according to claim 1 wherein the aqueous fluid contains substantial quantities of dissolved inorganic or organic materials.

* * * * *